(12) United States Patent
Newberg et al.

(10) Patent No.: US 7,241,422 B2
(45) Date of Patent: *Jul. 10, 2007

(54) HOUSING FOR RECEPTABLE FILLING

(75) Inventors: Douglas A. Newberg, Gambrills, MD (US); Richard R. Newberg, Gambrills, MD (US)

(73) Assignee: NL Technologies, Ltd., Gambrills, MD (US)

(*) Notice: Subject to any disclaimer, the term of this patent is extended or adjusted under 35 U.S.C. 154(b) by 793 days.

This patent is subject to a terminal disclaimer.

(21) Appl. No.: 10/199,114

(22) Filed: Jul. 22, 2002

(65) Prior Publication Data

US 2002/0182116 A1  Dec. 5, 2002

Related U.S. Application Data

(63) Continuation of application No. 09/247,526, filed on Feb. 10, 1999, now Pat. No. 6,423,548.

(60) Provisional application No. 60/074,205, filed on Feb. 10, 1998.

(51) Int. Cl.
*B01L 3/00* (2006.01)
*B65D 39/08* (2006.01)
*B65D 51/18* (2006.01)

(52) U.S. Cl. .................. 422/102; 422/99; 422/104; 422/58; 215/213; 215/217; 215/218; 215/219; 215/220; 215/221; 215/222; 220/256; 220/260

(58) Field of Classification Search ............... 422/99, 422/102, 104, 58, 63, 68.1; 220/256, 260; 215/213–215, 217–222
See application file for complete search history.

(56) References Cited

U.S. PATENT DOCUMENTS 4,160,382 A   7/1979   Finsterwalder et al.

(Continued)

*Primary Examiner*—Brian R. Gordon
(74) *Attorney, Agent, or Firm*—Birch, Stewart, Kolasch & Birch, LLP (57) ABSTRACT

A method and apparatus for capturing a sample of flowable material from a closed system inside a receptacle without exposing the sample to the ambient environment. The apparatus includes a housing having an opening at one end for receiving a receptacle and stopper. An end cap is removably mounted to the housing for opening and closing the opening. An inlet is provided in the housing for feeding a cleaning or sterilizing agent or the flowable material to be sampled into an interior of the housing. A clasp is provided to manipulate the receptacle to separate the receptacle and the stopper while the stopper and receptacle are inside of the housing. Once the receptacle and the stopper are separated, the flowable material is fed into the receptacle through the inlet. The clasp is then manipulated to reattach the receptacle and the stopper in order to capture the flowable material. The apparatus is particularly useful in the pharmaceutical and biotechnology industries as well as the fine chemical, food and beverage industries where accurate, uncontaminated samples of materials from a closed system are desired without contaminating the sample of material or the closed system.

8 Claims, 5 Drawing Sheets

U.S. PATENT DOCUMENTS

| | | |
|---|---|---|
| 4,526,045 A | 7/1985 | Reekie |
| 4,883,641 A | 11/1989 | Wicks |
| 5,152,500 A | 10/1992 | Hoobyar et al. |
| 5,154,188 A * | 10/1992 | Ebert ......................... 128/898 |
| 5,167,929 A * | 12/1992 | Korf et al. .................. 422/102 |
| 5,192,439 A * | 3/1993 | Roth et al. .................. 210/485 |
| 5,296,197 A | 3/1994 | Newberg et al. |
| 5,372,782 A | 12/1994 | Karkantis et al. |
| 5,409,841 A | 4/1995 | Chow |
| 5,525,301 A | 6/1996 | Newberg et al. |
| 5,725,832 A * | 3/1998 | Gundelsheimer ........... 422/102 |
| 5,783,155 A | 7/1998 | Greenler et al. |
| 5,786,209 A | 7/1998 | Newberg |
| 5,853,600 A * | 12/1998 | McNeal et al. ............. 210/789 |
| 5,871,700 A | 2/1999 | Konrad |
| 6,258,323 B1 * | 7/2001 | Hormann et al. ............. 422/99 |
| 6,827,904 B2 * | 12/2004 | Kitagawa .................... 422/100 |
| 6,878,340 B2 * | 4/2005 | Heath et al. .................. 422/63 |
| 2002/0041830 A1 * | 4/2002 | Newberg .................... 422/100 |
| 2003/0129765 A1 * | 7/2003 | DiCesare et al. ........... 436/172 |
| 2003/0215362 A1 * | 11/2003 | Sato et al. .................... 422/63 |
| 2004/0126278 A1 * | 7/2004 | Takahashi et al. ............. 422/99 |
| 2004/0170532 A1 * | 9/2004 | Takahashi et al. ............. 422/99 |

* cited by examiner

HOUSING FOR RECEPTABLE FILLING

This application is a continuation of application Ser. No. 09/247,526, filed on Feb. 10, 1999, now U.S. Pat. No. 6,423,548, the entire contents of which are hereby incorporated by reference and for which priority is claimed under 35 U.S.C. § 120; and this application claims priority of application Ser. No. 60/074,705 filed in the United States on Feb. 10, 1998 under 35 U.S.C. § 110.

BACKGROUND OF THE INVENTION

1. Field of the Invention

The present invention relates to a device for capturing a sample of flowable material from a closed system inside a receptacle without exposing the sample to the ambient environment. The present invention would find broad application in the pharmaceutical and biotechnology industries as well as the fine chemical, food and beverage industries where obtaining accurate, uncontaminated samples of process flows from closed systems while maintaining the integrity of those systems and/or the sample is important 2. Description of the Background Art Development of new or more efficient commercialization of existent products requires faster and more effective methods to measure process variables. This is particularly true in processes which require cell culture and fermentation processes conducted in bio-reactors where the accuracy of measurements and research and development are critical for achieving economic production of high purity and highly refined end products.

Some factors which must be controlled include temperature and pressure. These factors are easily measured by utilization standard sensors. However, many other factors can be measured only by removing samples for external laboratory analysis. The frequency of sample extraction for testing and measurement, the number of tests on each sample, and the time constraints on the process vary widely as do the methods and equipment used to obtain the samples.

In most cases, measurement processes for variables do not lend themselves to in-situ measurement by remote sensors directly in the process. Instead, samples must be physically extracted from the processes and examined and manipulated outside the vessel or conduit. Before this examination and manipulation process can be effectively carried out either in a manual or an automated fashion, a safe, effective means of sample extraction must be made available. This sampling process must provide a product that is an accurate sub-sample of the process composition.

Furthermore, since prior art designs do not lend themselves to use in existing systems, substantial modification to the system is required. The apparatus needs to minimize or eliminate the dangers associated with the sampling process in an efficient and cost effective manner, while providing quality, reproducible results in order to be of value for commercial application.

One danger which must be avoided is danger to the operator or environment. When working with samples and especially hazardous samples, it is necessary to remove or feed/inoculate a sample without endangering the integrity of the process, subsequent samples, the operator, or the outside environment. Many prior art devices are unsatisfactory in this area.

Some prior art systems are not automated. Therefore, there is potential danger posed by human procedural errors and operator and environmental exposure. Accordingly, a need exists for an automatable apparatus with a capacity for independent verification of equipment operation built in.

In some cases, the materials being sampled are often expensive. Therefore, excessive removal of a sample should be avoided.

When taking samples, it is often important to maintain an aseptic environment. It is important that contamination from previous sampling or from the environment not contaminate the current sample or the process being sampled. Loss of a sample run or contamination of the process can have extremely expensive ramifications. Therefore, it is important to obtain a sample without the sampling procedure causing contamination.

Many prior art devices permit accumulation or pooling of samples or cleansing medium. When the device is first used it may not create a problem; however, upon subsequent runs, the samples will be contaminated or at least diluted.

The Disclosures of U.S. Pat. Nos. 5,296,197, 5,525,301, and 5,786,209 relate to automated sample extractors or feeder/inoculates for bio-reactors and similar equipment. The Disclosures of these patents are hereby incorporated by reference.

The above-mentioned patents relate to removing a sample from a vessel or conduit without contamination of the sample, process, or surrounding environment. The present invention is usable with devices of this type or with similar devices. Namely, once the sample is removed from the vessel or conduit, it becomes necessary to feed the sample into a receptacle for later processes or testing.

In the past, sampling from a vessel or conduit was performed by hand by an operator. This manual sampling ran the risk of exposure to dangerous substances by the operator as well as contaminating the sample.

SUMMARY OF THE INVENTION

Accordingly, it is a primary object of the present invention to provide a simple, reliable, safe, and cost effective means for capturing a sample of flowable material from a closed system inside a receptacle and stoppering the receptacle without exposing the sample or the material to the surrounding outside environment.

It is another object of the present invention to capture a sample of flowable material from a closed system inside a receptacle without subjecting an operator to dangerous substances.

It is a further object of the present invention to capture a sample of flowable material from a closed system in order to obtain sterile samples which can be kept pure for a longer period of time.

It is yet a further object of the present invention to provide an apparatus which can be retrofitted to existing standard equipment without substantial modification.

It is yet another object of the present invention to provide an apparatus which will conduct sampling and maintain the sample in a sealed arrangement such that there is no danger to the sample itself to the operator, to the process, or to the surrounding environment.

It is yet another object of the present invention to provide a device which can protect an operator from the sampled material by isolating it in a container, whether or not maintaining the integrity of the process or sample itself is important.

It is a further object of the present invention to provide an automatable system in order to eliminate possible operator error.

It is a further object of the present invention to provide a receptacle for collecting a sample within a sealed environment so that the area approximate the receptacle can be cleansed or sterilized and therefore be kept free from contaminates. The receptacle can be a receptacle and stopper combination, and the stopper can be removed within the cleansed or sterilized environment, the receptacle can be filled with the sample, and the stopper can be reattached to the receptacle all within the cleansed or sterilized environment.

It is a further object of the present invention to allow the receptacle and/or stopper to be washed, rinsed, disinfected, and/or sterilized in place using any of a variety of flowable materials at ambient, reduced, or elevated temperatures.

Another object of the present invention is to provide an apparatus which can be repeatedly cleaned and/or sterilized in place.

Yet another object of the present invention is to provide an apparatus which can be easily removed and quickly disassembled for maintenance, including replacement of worn parts.

A further object of the present invention is to provide an apparatus made of materials which are compatible with the sample materials and the process.

Still another object of the present invention is to provide an apparatus which will be reliable, easy to maintain, and low in cost.

These and other objects of the present invention are fulfilled by providing an apparatus for capturing a sample of flowable material from a closed system inside a receptacle and stopping the receptacle without exposing the sampled material to the surrounding outside environment.

The device for sampling flowable material includes a housing for receiving a receptacle therein. This housing includes an end-cap removably mounted to the housing for allowing a receptacle to be inserted into the housing and removed therefrom. The housing also includes an inlet formed therein for receiving flowable materials therethrough. The inlet includes means for cleaning at least a portion of the housing proximate to the receptacle attached thereto. The means for cleaning is operable when the end-cap is mounted on the housing. Finally, a clasp is mounted within the housing for engaging the receptacle.

The present invention also includes a method of sampling flowable material. This method includes inserting a receptacle into a housing, closing the housing to seal the receptacle from the ambient environment, sterilizing the inside of the housing, filling the receptacle with flowable material, opening the housing, and removing the receptacle.

The inserting of the receptacle into the housing can include inserting a receptacle with or without a stopper connected thereto. If the receptacle is inserted with a stopper connected thereto, an additional step of removing the stopper while the receptacle and stopper are within the housing would be necessary. If a receptacle is inserted with the stopper detached, it is unnecessary to include the step of removing the stopper. If the method of the present invention includes a stopper connected to the receptacle stopper, the removing of the stopper while inside the housing can include the steps of gripping the receptacle, rotating the receptacle to remove the stopper from the receptacle, and longitudinally moving the receptacle with respect to the stopper in order to space the receptacle from the stopper.

In either of the above two embodiments, the method of the present invention can also include the step of reattaching the stopper after filling of the receptacle with the flowable material.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

Referring in detail to the drawings and with particular reference to FIGS. 1–4, a housing 1 according to the present invention is designed to accept a stoppable receptacle or sample tube 3, and a stopper or sample tube cap 5. It is noted that the same reference numerals are used throughout the several views to identify the same elements.

A first embodiment of the present invention will now be described with reference to FIG. 1. The housing 1 of the present invention includes a head plate 7 and a drain plate 9. A sight tube 11 is secured between the head plate 7 and the drain plate 9 by a plurality of longitudinally extending bolts 13. The sight tube 11 is made of glass or clear plastic to enable viewing of the receptacle from an outside of the housing 1. A head gasket 8 is inserted between the sight tube 11 and the head plate 7 and a base gasket 10 is inserted between the sight tube 11 and the drain plate 9. The bolts 13 are secured to the head plate 7 by welding or by threading the bolt into the head plate 7. The bolts 13 extend from the head plate 7 through apertures 15 formed in the drain plate 9. Free ends 17 of the bolts 13 extend from a lower surface 19 of the drain plate 9. Nuts 21 are attached to the free ends 17 of the bolts 13 in order to secure the drain plate 9 to the head plate 7, and the sight tube 11 between the head plate 7 and the drain plate 9. It is noted that the above-described arrangement for connecting the head plate and base plate with the sight tube is not the only arrangement that can be used. It is only necessary that the arrangement securely connect the head plate and the base plate with the sight tube to provide a sealed environment inside.

The head plate 7 includes an inlet 23 for receiving the flowable material. The inlet receives a threaded o-ring connector 24 including a connecting portion 25 and an o-ring 26. This threaded o-ring connector 24 is connectable to a sample valve (not shown) which in turn would be connected to a vessel or conduit from which a sample is to be obtained. The flowable material to be sampled can be fed from the sample valve to the inlet 23 in order to fill the receptacle with the flowable material. Furthermore, a cleaning or sterilizing agent can also be fed from the sample valve in order to wash, rinse, disinfect, and/or sterilize an interior of the housing 1 and its contents.

The head plate 7 also includes a through-hole 27a formed therethrough. An opening 27 of the through-hole 27a is formed at an upper part thereof for providing access to an interior of the housing 1. A shoulder 29 is formed at the opening 27 in order to receive the stopper 5 of the receptacle 3. An aperture or hole 31 is formed at a lower portion of the through-hole and extends from the shoulder 29 through the head plate 7. This aperture or hole 31 is preferably sized having an inside diameter larger than the diameter of the receptacle 3, but smaller than the diameter of the stopper 5.

It is noted that capturing stopper 5 between shoulder 29 and end cap 33 is one way of immobilizing stopper 5 so that, when the receptacle is rotated, the two can be disengaged from and re-engaged to each other. Alternative embodiments to immobilize stopper 5 relative to receptacle 3, including pins extending part way into through-hole 27a, a tight fit between the outside diameter (OD) of stopper 5 and the inside diameter (ID) of the through-hole 27a in head plate 7, or a tight fit of the OD of the stopper 5 with the ID of a recess with the end cap 33 would serve equally as well. It is only important that the stopper 5 be immobilized relative to the receptacle 3. This will be further described below.

The head plate 7 also includes a passageway 30 formed therethrough. The passageway 30 longitudinally extends from the shoulder 29 through the head plate 7 to a lower surface 28 of the head plate 7. A portion of the passageway 30 adjacent the shoulder 29 includes a recessed portion 32 which enables communication between a top of the stopper 5 and a bottom of the stopper 5. The passageway 30 allows communication from the shoulder 29 to the lower surface 28 of the head plate 7, the lower portions of housing 1 and outlet 35. The combination of the recessed portion 32 and passageway 30 allows the flow of air, cleaning and sterilizing agents all around stopper 5 as well as between inlet 23 and all spaces within the housing 1 below the lower surface 28 to outlet 35. This is important particularly in cases where the OD of the receptacle 3 is substantially the same as the ID of the aperture 31, creating an unpasssable seal which, without recessed portion 32 and passageway 30, would result in a vapor lock and inhibit drainage into and out of housing 1 and material flowing into the receptacle 3.

An end cap or house cap 33 is removably mounted to the head plate 7 adjacent to the opening 27. An o-ring 34 is inserted between the end cap 33 and the housing 1 in order to provide a sealed connection. FIG. 1 illustrates a threaded connector 36 on the end cap 33 and a cooperating threaded portion 38 on the inside of the opening 27 of the head plate 7; however, any fastener which allows easy attachment and detachment of the end cap from the housing and which allows the housing to be sealed from the ambient environment will suffice. Alternative end cap constructions will be described below.

The above-described arrangement provides a sealed environment within the housing 1 which is protected from the ambient environment when the end cap 33 is properly secured and the inlet 23 and outlet 35 are connected to a process by some means.

With regard to the drain plate 9, an outlet 35 is provided for receiving a drain connector 37. The outlet 35 allows a cleaning agent or sterilizing agent or excess flowable material to be removed from the interior of the housing. A threaded o-ring connector 40 including an o-ring 42 and a drain connecting portion 44 is connected to the outlet 35. The drain connecting portion 44 is connectable to a drain assembly 46 such as the threaded drain block 48 and the threaded o-ring connector 50 in FIG. 1 in order to connect the outlet 35 to a drain (not shown). The drain plate 9 also includes an aperture 39 formed therethrough for receiving a rod 41. A plurality of O-rings 45 are inserted within the aperture 39 between the aperture 39 and the rod 41 in order to seal an interior of the housing from the ambient environment. The rod 41 includes a knob 43 for manipulating the rod 41. The rod 41 is mounted in the drain plate for longitudinal and rotary motion.

The knob 43 is connected to a first end of the rod 41 outside of the housing 1. A pedestal 47 is attached to a second end of the rod 41 within the interior of the housing 1. The pedestal 47 includes a first open end 51 remote from the rod 41 and a second closed end 52 proximate the rod 41. The pedestal 47 is a generally cylindrical member which has a tapered portion 53 adjacent to the rod 41. The tapered portion 53 is only needed if the upper face of the drain plate is tapered, allowing the two to be mated together, maximizing the longitudinal range of motion of the rod-pedestal combination within the housing 1.

A plurality of longitudinal openings 55 are provided for allowing viewing access of the stopper or receptacle 3 from the outside of the housing. The open end 51 of the pedestal 47 includes an o-ring 49 for gripping a body of the receptacle when the pedestal is moved into contact with the receptacle 3.

Figure 5:
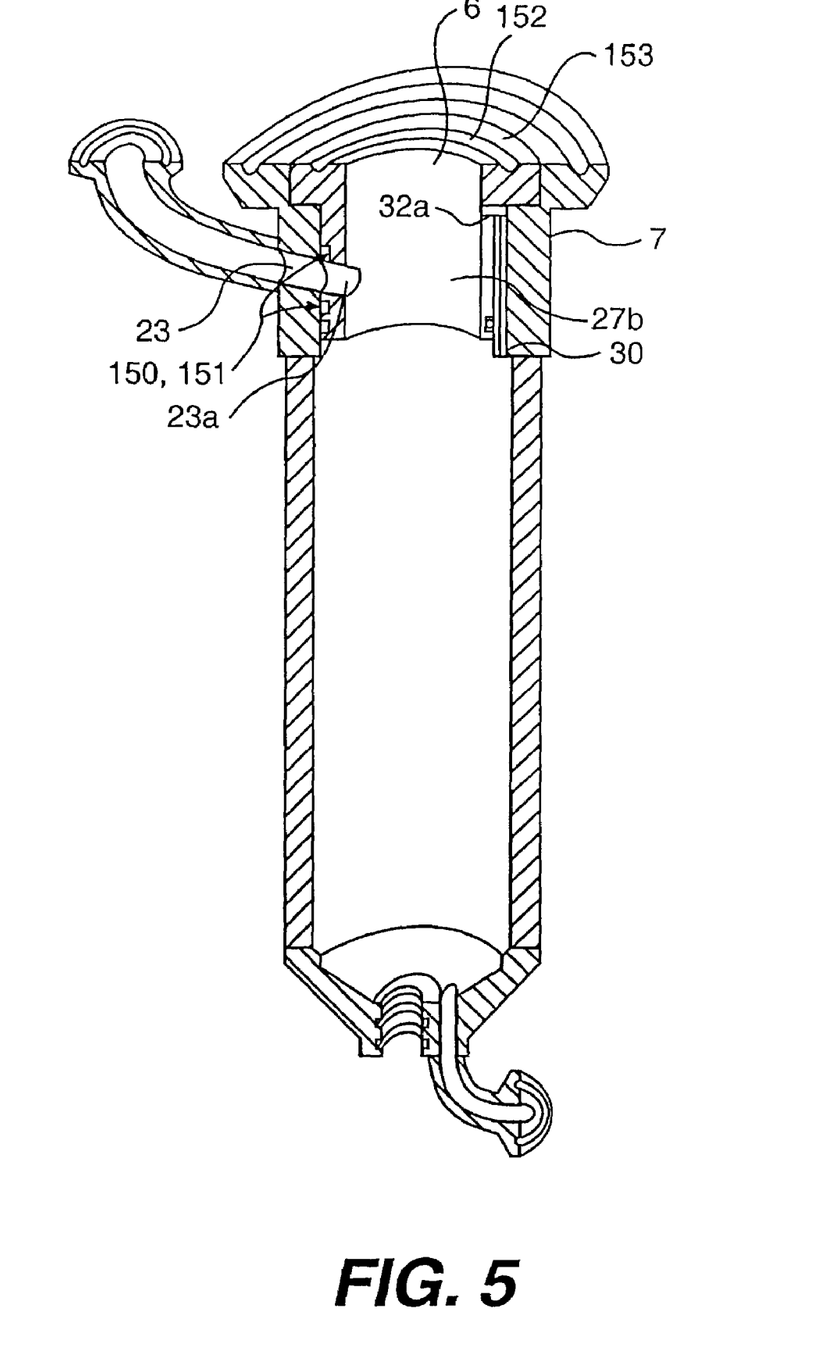
FIG. 5 is a cross-sectional view of an insert of the present invention.

Referring to FIG. 5, in order to accommodate receptacles of various sizes, it is possible to provide an insert 6 within the opening 27 and the through-hole 27a in order to vary the diameter of the aperture 31. Varying the diameter of the aperture 31 allows receptacles of different diameters or capacities to be used in the same housing. Referring to FIG. 5, insert 6 has an outside profile that mates with the ID profile of the opening 27 and the through-hole 27a. This insert 6 includes an inlet 23a that aligns with the inlet 23 and allows flowable materials coming in through inlet 23 to be fed into the through-hole 27b of the insert 6. As with head plate 7, insert 6 is sized with a diameter larger than the OD of a smaller receptacle 3, but insert 6 need does not have a shoulder. The stopper 5 is merely tightly fit in the through-hole 27b. A shoulder is not necessary as long as the insert 6 is capable of holding the stopper 5 immobile relative to the receptacle 3. However, the insert 6 may have shoulder if desired. Insert 6 also has an o-ring 150 fitted with an o-ring groove 151 in its OD wall about the inlet 23a where it mates with inlet 23, forming a seal around the junction between the two. Insert 6 has a further o-ring groove/o-ring combination or gasket 152 at its lower OD margin that seals the crevice between insert 6 and the aperture 31 from the inside of the housing 1. Insert 6 has a radial groove/hole combination 32a that aligns with recess portion 32 described below for venting. The top surface 153 of the insert 6 seals with an end cap 33 in the same manner as the head plate 7. Furthermore, if the head plate 7 does not have a shoulder 29 to keep insert 6 from slipping through the through-hole 27, insert 6 may be modified to include an annular lip, for example, in order to prevent it from slipping through.

An operation of the first embodiment of the present invention will now be described. The threaded o-ring connector 24 which is attached to the inlet 23 can be attached to the sample valve either before or after the receptacle is inserted in to the housing 1. The end cap 33 is first removed from the housing 1 to gain access to the interior of the housing 1. The receptacle 3 is inserted into the interior of the housing with the stopper attached thereto or with the stopper separate therefrom. The stopper 5 is positioned to rest on the shoulder 29 of the head plate 7, while the receptacle 3 extends through the aperture 31 formed in the head plate 7. Once the receptacle 3 and the stopper 5 are properly located, the end cap 33 is secured to the housing 1 in order to seal the receptacle and stopper within the housing 1 and from the ambient environment. With the securing of end cap 33, stopper 5 becomes immobilized between the shoulder 29 and the end cap 33.

At this point, a cleaning or sterilizing agent is fed through the inlet 23 of the head plate 7 from the sample valve. The cleaning or sterilizing agent flows into the interior of the housing and out the outlet 35 formed in the drain plate 9. This cleaning or sterilizing agent cleans or sterilizes an interior of the housing 1 and an exterior of the receptacle 3 and stopper 5 if the stopper is secured in place on the receptacle. Otherwise, the agent cleans both the inside and the outside of the stopper 5 and the receptacle as well as all of the remaining portions of the inside of the housing 1 and flow lines leading to and from the housing. This provides a clean environment for ensuring that the flowable sample is not contaminated during filling of the receptacle. Once the cleaning and sterilizing operation is performed, the knob 43 is manipulated to move the rod 41 and the pedestal 47 longitudinally upward into engagement with the receptacle 3. Once the o-ring 49 is in proper engagement with the receptacle 3, the knob 43 is rotated to rotate the rod 41 and pedestal 47 in order to remove the receptacle 3 from the stopper 5. It is necessary to rotate the receptacle 3 one to one-and-one-half turns in order to remove the receptacle from the stopper 5 if a typical screw-type receptacle-stopper combination is used. It should be noted that, with an o-ring 45, pedestal 47 may be continuously rotated as many times as necessary to unscrew the stopper 5 from the receptacle 3. However, if the seal between the drain plate 9 and the pedestal-rod combination is made using a diaphragm, as will be described in a later embodiment, the range of rotation of the pedestal-rod combination will be limited. The stopper and the receptacle may still be unscrewed from each other; however, simply by first rotating the pedestal-rod combination as far as possible in the thread-tightening direction, engaging the receptacle, and rotating the pedestal-rod-receptacle combination as far as possible in the opposite thread-loosening direction before disengaging the receptacle. If the stopper is not unsrewed from the receptacle at this time, the pedestal-rod combination can be rotated as far as possible in the thread-tightening direction, and the receptacle can be engaged again and rotated further in the thread-loosening direction. This can be repeated until the stopper 5 can be separated from the receptacle. To seal the receptacle after the sample is collected, the above procedure can be reversed. It is also possible to use a plunger-type receptacle-stopper combination. In this case, it is only necessary to use longitudinal motion of the pedestal to remove the stopper from the receptacle, since the stopper and receptacle are unthreaded; however, rotation of the pedestal can help to remove the stopper from the receptacle.

Once the receptacle 3 has been removed from the stopper 5, the knob 43 is manipulated to longitudinally move the rod 41 and pedestal 47 downward in order to space the receptacle 3 from the stopper 5. The receptacle 3 is moved downward to a location where an open portion of the receptacle is at or below a lower surface of the inlet 23. The flowable material is then fed from the sample valve into the inlet 23 and into the receptacle 3 to fill the receptacle 3 with a predetermined quantity of flowable material. When the flowable material is filled in the receptacle 3, the feed of flowable material is stopped and the knob 43 is manipulated to attach the receptacle to the stopper 5 in a reverse manner from removing the receptacle.

At this point, the cleaning or sterilizing agent can be re-fed through the housing 1 in order to clean the outside of the receptacle 3 or the end cap 33 can simply be removed without further cleaning or sterilizing in order to remove the stoppered receptacle from the interior of the housing. In situations where the flowable material to be sampled is dangerous to the operator, cleaning or sterilizing after filling would be advantageous to protect the operator.

During the above-mentioned operation of the first embodiment of the present invention, the receptacle and stopper are preferably inserted into the housing 1 in a connected condition. In this way, a pre-sterilized stopper and receptacle combination can be utilized. It is only necessary to clean or sterilize the outside surface of the receptacle and stopper, since the inside is already sterilized. Alternatively, a receptacle having a stopper detached therefrom can be inserted into the housing. In this situation, the knob 43 merely needs to be manipulated in order to grip the receptacle and longitudinally move the receptacle away from the stopper. This procedure is useful for stopper and receptacle combinations which are not sterilized previous to entering the housing 1. A gaseous sterilizing agent is especially useful for this purpose; however, if a liquid sterilizing agent is used, the housing merely needs to be turned upside down in order to remove the cleaning or sterilizing agent from the receptacle before filling.

A first embodiment of the present invention has been described with reference to FIG. 1. A second embodiment will now be described with reference to FIG. 2. FIG. 1 illustrates a pedestal 47 and O-ring 49 for gripping and manipulating the receptacle 3. Referring to FIG. 2, an alternative arrangement for manipulating the receptacle 3 is illustrated. A knob 43 is attached to a rod 41 in the same manner as that illustrated in FIG. 1. However, at a second end of the rod, a base 57 is attached instead of the pedestal 47. The base 57 includes a plurality of longitudinally extending, vertical support rods 59 attached thereto and extending upwardly toward the receptacle 3. The support rods 59 can be attached in ay manner including welding and a removable fastener. FIG. 2 illustrates the support rods 59 attached with a pin 60 driven through the base 57 and an end of the support rods 59. There are preferably three support rods; however, the number of support rods is not important as long as there is a sufficient number to grip the receptacle 3. The support rods 59 may have a modified surface, coating or cover that grips the receptacle, the contact area between these rods and the receptacle being at least significantly longitudinal in nature. This longitudinal contact area will assure that the pedestal-rod combination will grip and rotate the receptacle relative to the stopper with a minimal amount of slippage. The effect of increasing the longitudinal contact are a relative to the circumferential contact area will have the effect of making it easier to slip the pedestal-rod combination onto and off of the receptacle while reducing the slipping that occurs when rotating to thread the receptacle off and on the stopper threads, permitting tighter seals to be made. In this figure, each of the support rods 59 includes plastic tubes 61 secured thereon. Furthermore, an o-ring 63 is secured around the free ends 65 of the support rods 59. The o-ring 63 and plastic tube 61, provide gripping means for gripping the outside surface of the receptacle 3. The o-ring further provides added tension at the free ends 65 of the rods, reducing the deflection over time by providing a degree of positional memory to the free ends 54, a result of elastic "memory" of the o-ring.

This arrangement is operated in the same manner as the pedestal arrangement above. The knob 43 is manipulated to move the rod 41 and base 57 along with the support rods, plastic tubes, and O-ring to engage the outer surface of the receptacle 3. The knob 43 is then rotated in order to remove the receptacle 3 from the stopper 5 and longitudinally moved downward to separate the receptacle 3 from the stopper 5.

Figure 1:
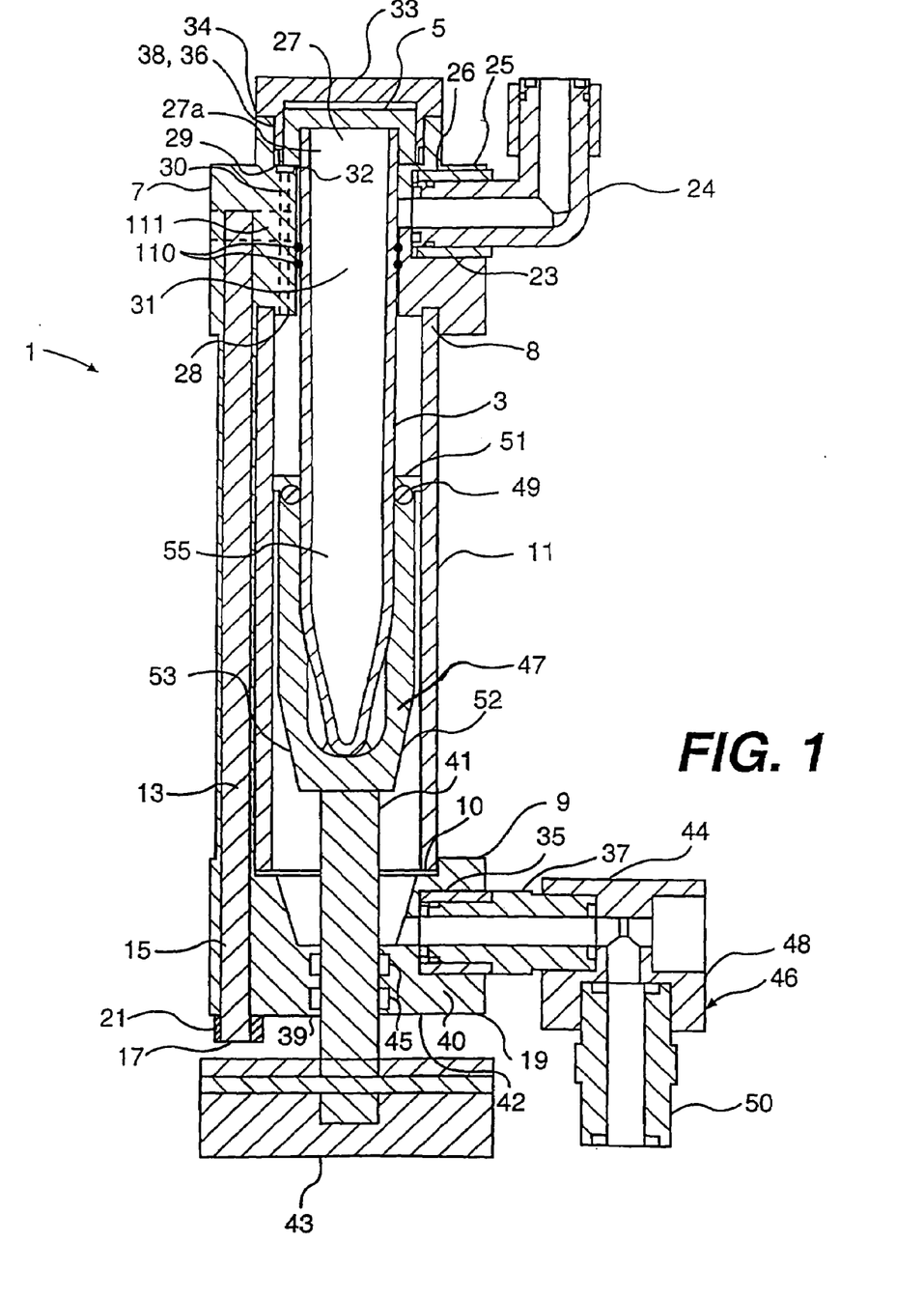
FIG. 1 is a cross-sectional view of the apparatus of the present invention according to a first embodiment.
Figure 2:
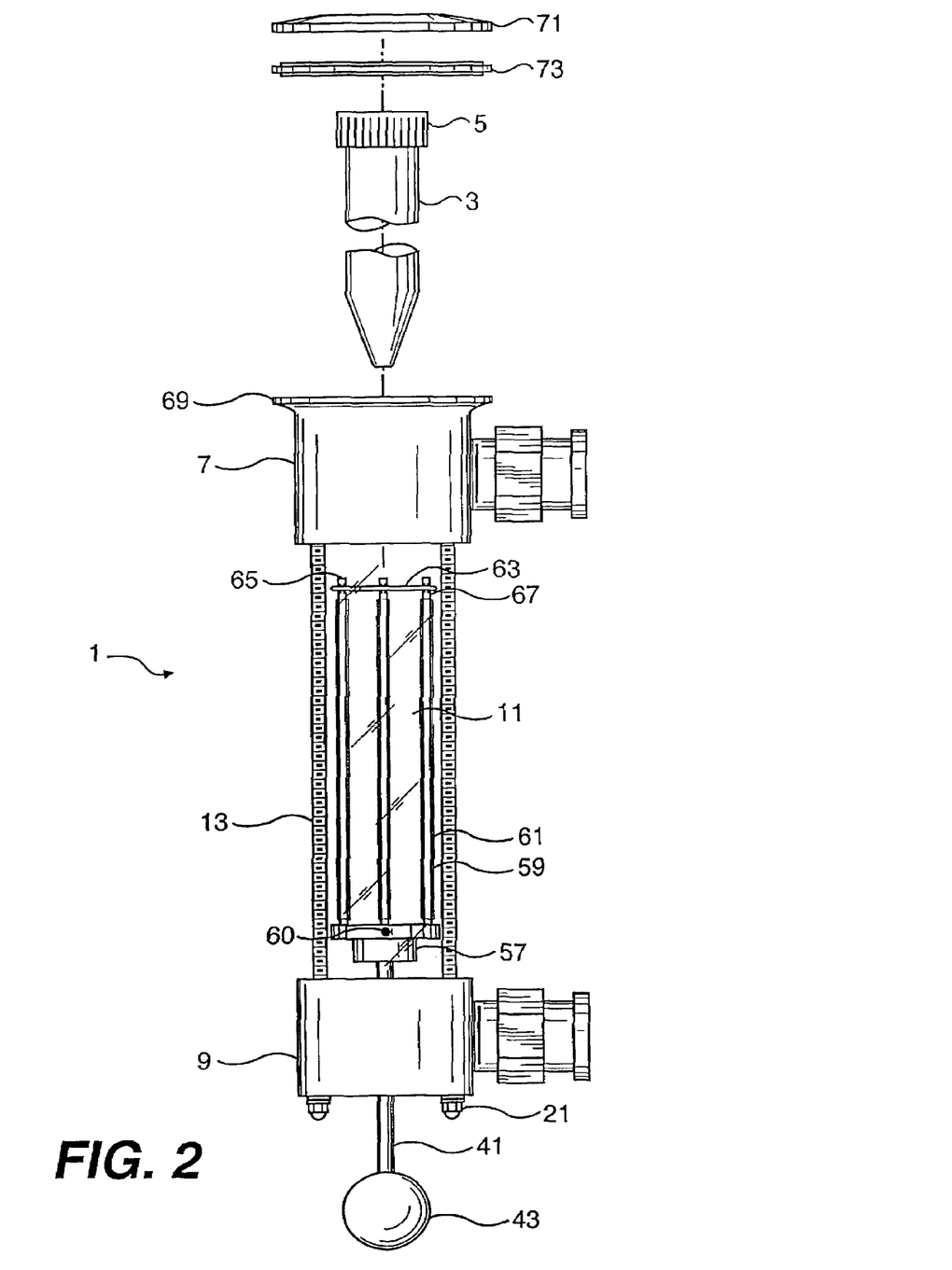
FIG. 2 is a perspective view showing the apparatus of the present invention in partially exploded form including a receptacle, a stopper, and an end cap detached from the housing according to a second embodiment.

The end cap 33 illustrated in FIG. 1 includes a threaded connector 36 for engaging with the threaded portion 38 formed in the head plate 7. However, referring to FIG. 2, the head plate 7 according to the second embodiment of the present invention may, in addition to the threaded portion 38, include a flange portion 69 at a top surface thereof. The head plates 7 in the first and second embodiments are substantially the same except for the addition of the flange portion 69 in the second embodiment. This flange portion 69 enables the alternative use of an end cap 71. The end cap 71 is engageable with the flange portion of the head plate 7 with a gasket 73 inserted therebetween. The end cap 71 can be attached to the flange portion 69 with a conventional clamping arrangement (not shown). A clamping arrangement of this type is well known and will not be further described here. The gasket 73 ensures that the end cap 71 seals the receptacle 3 within the inside of the housing 1 and from the ambient environment.

It is reiterated that the head plate 7 according to the second embodiment can include both the threaded portion 38 and the flange portion 69 in order to allow either a flange-type end cap 71 or a threaded-type end cap 33 to be used with the head plate 7. However, the threaded portion 38 is not required in the second embodiment.

Figure 3:
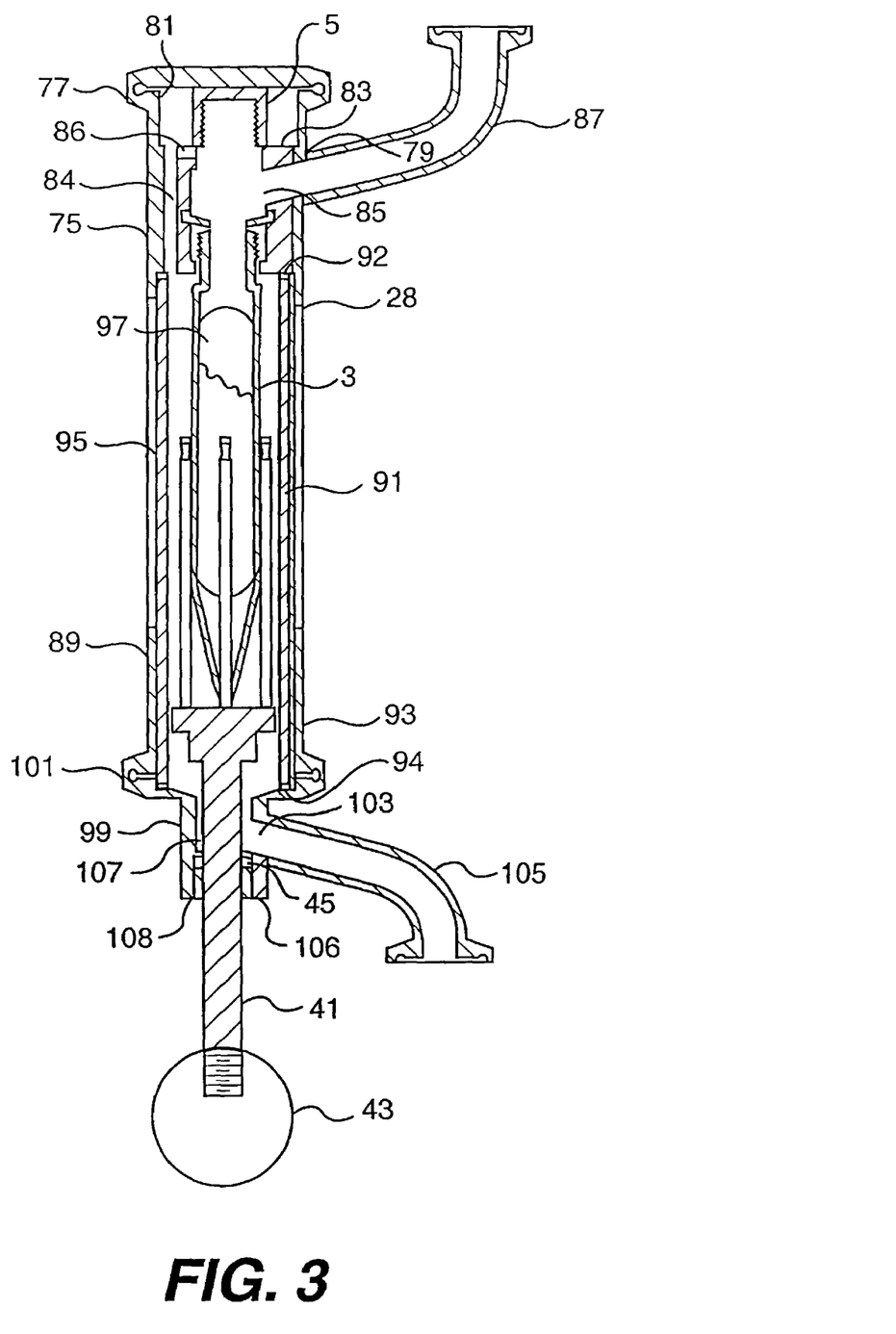
FIG. 3 is a cross-sectional view of the apparatus according to a third embodiment of the present invention.

A third embodiment of the present invention will now be described with reference to FIG. 3. FIG. 3 illustrates an alternative housing 1 according to the present invention. A head plate 75 includes a flange portion 77 formed on a first end thereof and a threaded portion 81 formed within an open end 82 of the head plate 75. A shoulder 83, passageway 84, recessed portion 86, and aperture 85 are substantially the same as those in the first embodiment. An inlet 79 includes an elbow 87 preferably welded thereto instead of the threaded oaring connector 24 in the first and second embodiments. This elbow 87 is connectable to a sample valve as in the first and second embodiments and operates in substantially the same manner.

The head plate 75 also includes a generally cylindrical tube 89 formed on a second end thereof. The generally cylindrical tube 89 extends away from the head plate 75 and attaches to a base plate 93. A sight tube 91 is secured within the generally cylindrical tube 89 between the head plate 75 and the base plate 93. A head gasket 92 and a base gasket 94 are inserted at the ends of the sight tube 91 adjacent the head plate 75 and the base plate 93, respectively. The generally cylindrical tube 89 includes a plurality of longitudinal openings 95 for allowing the interior sight tube 91 and receptacle 3 to be viewed therethrough. New techniques now permit glass sight tubes to be welded directly to other materials, including stainless steel. Consequently, the bolts, clamps and gaskets used to connect the head plate, drain plate and sight tube together and the gaskets used to form seals to seal the system from the surrounding environment may be eliminated as is illustrated in FIG. 5. Slipping a mesh screen over the housing 1, particularly the glass portion, may still be desirable. This will provide the housing with a degree of protection from outside impacts and will provide protection to operators in the area should the sight tube fail.

In some cases it may be advantageous to automate the system. Automation would include a device to automatically control sample volume fed to the housing 1. Automated measurement would eliminate the need for operators to visually monitor the instantaneous volume of a sample in the receptacle. Consequently, the sight tube may be eliminated and the housing may be made without apertures in the housing walls. In fact, the head plate, drain plate and tube connecting the two could be fabricated from a single piece of material.

A mesh screen 97 (illustrated partially broken away) is secured over the longitudinal openings 95 in order to protect the sight tube 91 from external impact. The mesh screen 97 can be attached to the edges of the longitudinal openings in the generally cylindrical tube 89 or can be secured between the generally cylindrical tube 89 and the sight tube 91. The mesh screen 97 can be extended around a portion of the circumference of the generally cylindrical tube 89 or can extend completely around the circumference of the generally cylindrical tube 89.

The base plate 93 is in the form of a flange which is engageable with a drain member 99 having a flange 101 formed on an upper portion thereof. The flange 101 of the drain member 99 and the base plate 93 are connectable together by a clamp (not shown). The drain member 99 includes an outlet 103 having an elbow 105 welded thereto. The drain member 99 also includes an aperture 107 extending therethrough. The aperture 107 is connected to the outlet 103 and also extends to a lower surface 106 of the drain member 99. The lower end 108 of the aperture 107 also includes the typical o-rings 45 secured therein and a rod 41 supported thereby as in the previous embodiments.

The third embodiment of the present invention is usable with the pedestal 47 of the first embodiment or the base 57 and the vertical support rods 59 of the second embodiment. The head plate 75 of the third embodiment is usable with either of the end caps 33 or 71 of the first and second embodiments.

The third embodiment is advantageous since the assembly and disassembly of the housing is improved. It is only necessary to remove a single clamp which secures the flange 101 to the base plate 93 rather than removing several of the bolts 13 as in the first embodiment.

Figure 4:
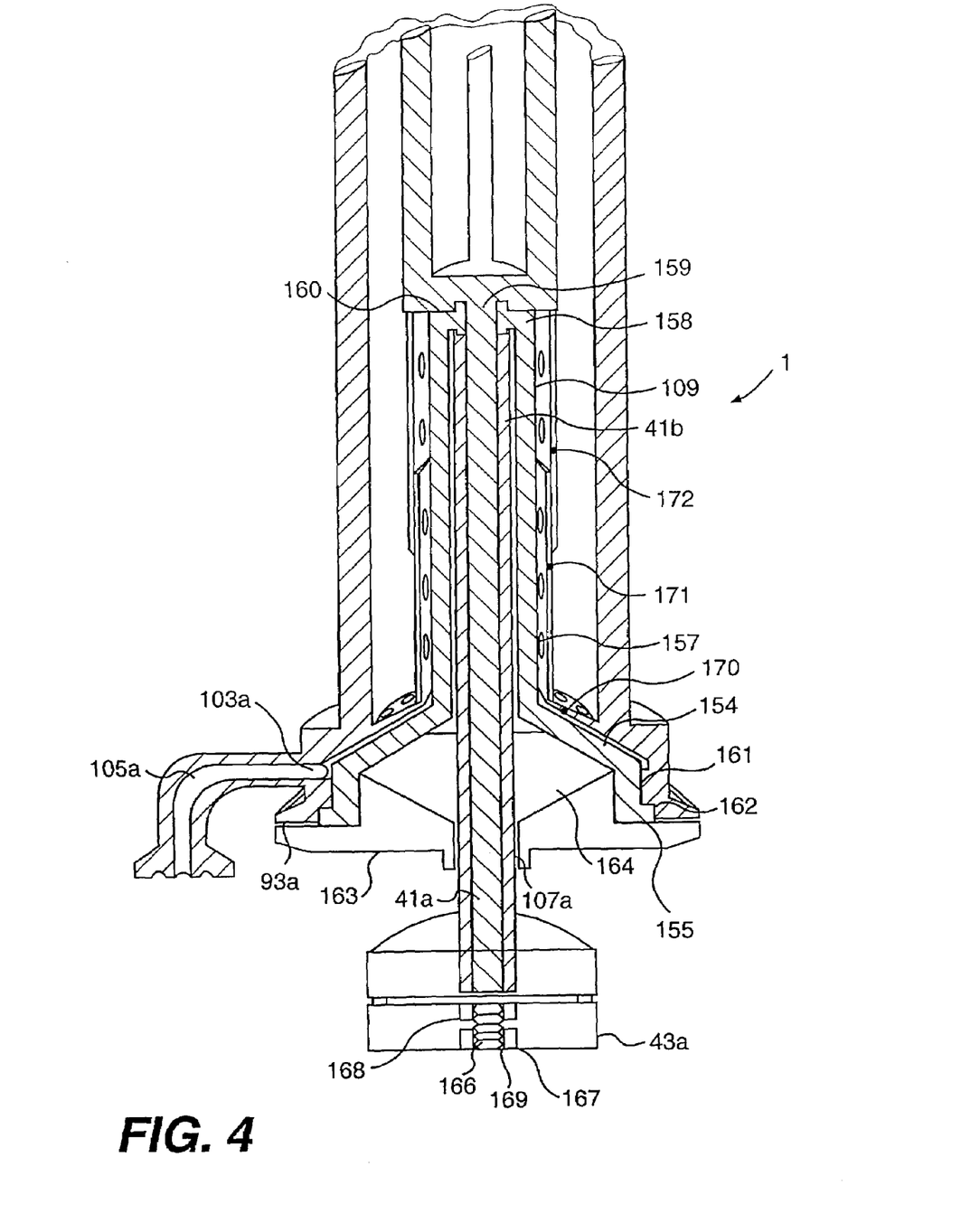
FIG. 4 is a cross-sectional view illustrating an alternative sealing arrangement of the present invention.

An alternative arrangement to seal between the rod 41 and the drain member 99 of the third embodiment will now be described with reference to FIG. 4. Instead of the o-rings 45 secured within the drain member 99, a diaphragm 109 can be included in its place. The diaphragm 109 includes a base 155 with a sealing face 161 and an annular lip 162, a conical section 154, a narrow elongated tubular section 157, a blunt tip 158 with a through-bore 159 and an upper sealing face 160. Diaphragm base 155 can be fitted into a flanged base plate 93a having an opposing mating contour as shown in FIG. 4. Flanged base plate 93a has an outlet 103a having an elbow 105a welded thereto for drainage of the housing 1. An opposing flanged base plate 163 mates with flanged base plate 93a, capturing the annular-cylindrical section of the diaphragm base as shown in FIG. 4. Flanged base plate 163 has a conical counter bore 164 and a central longitudinal through-bore 107a to receive the flexing cone portion 154 and the rod 41a and rod sleeve 41b. Rod 41a is inserted through the through bore 159 in the blunt tip 158 of diaphragm 109 until it extends out the conical section 154 and out through flanged base plate 163. Sleeve 41b is slipped over the threaded tip 166 of rod 41a and pushed all the way up until its upper face engages the back wall to upper sealing face 160. Threaded tip 166 and sleeve 41*b* are slipped into the central through-bore 167 of knob 43*a*. Sleeve 41*b* will engage a shoulder 168 while threaded tip 166 will continue all the way through and protrude to the bottom of knob 43*a* where a nut 169 will be threaded on to it. As nut 169 is tightened, it will cause blunt tip 158 to be compressed by the upper end of sleeve 41*b* and cause a seal to be made between the bottom of the pedestal and upper sealing face 160. Thus static seals are created at ends of the diaphragm 109, isolating the inside of housing 1 from the surrounding environment even when the pedestal is moved up and down to engage and disengage receptacle 3 and when the pedestal is rotated to unthread and rethread stopper 3 with receptacle 3.

FIG. 4 illustrates an upper conical section 170 with an attached cylindrical section 171 that may be incorporated as part of flanged base plate 93*a*, surrounding the conical portion 154 and the lower section of tubular portion 157 of diaphragm 109. An opposing cylindrical section 172 would extend down from the base of pedestal 47, enclosing the upper portion of tubular portion 157. These two cylindrical sections, while being of greater diameter than tubular portion 157, are of unequal diameters, allowing the overlapping portion of one to nest within the other. Parts 170, 171 and 172 in concert with conical counter bore 164, form a protective shroud around diaphragm 109. While this shroud may not be necessary if housing 1 is always properly vented so that it never becomes negative relative to the surrounding atmosphere or if the diaphragm is constructed of material strong enough to withstand the pressure differentials, in cases where it is not vented or the material is week, the shroud will prevent the diaphragm from ballooning, supporting it and keeping it from busting. In order to better circulate cleansing and sterilizing materials and to promote drainage, parts 170, 171, and 172 may be perforated as, for example, is illustrated in FIG. 4.

The diaphragm 109 can also be used with the drain plate 9 of the first and second embodiments as well. The diaphragm 109 merely secures within the aperture 39 in the drain plate 9 and extends along the rod 41 to be secured at the junction between the rod 41 and the pedestal 47 or the junction between the rod 41 and the base 57.

Referring again to FIG. 1, it is also possible to provide o-rings 110 within the aperture 31 and a drain opening 111 in the head plate 7. This will allow the cleaning or sterilizing agent to flow only in the top portion of the housing 1. The cleaning or sterilizing agent can flow through the inlet 23 and into the top portion of the interior of the housing 1 and exit through the drain 111. The o-rings prevent the cleaning or sterilizing agent from entering the bottom portion of the interior of the housing 1. Therefore, the outlet 103 is unnecessary, but may still be provided in case any excess material flows past the o-rings 110. It is noted that this arrangement is also usable with the second and third embodiments as well.

In any of the above-described embodiments, the housing is preferably constructed of stainless steel; however, it may also be constructed of other materials including polymers depending upon the application.

While the present invention has been described as being manually operated, automation may be achieved to a greater or lesser extent by modifying the system to include automated operators.

The present invention may also be modified to include a mechanism for longitudinally moving and axially rotating the stopper rather than the receptacle. Alternatively, the motions may be split so that both the stopper and the receptacle move. The way in which the receptacle is moved with respect to the stopper is not important as long as the receptacle and stopper (unless a receptacle without a stopper is desired in the end) are separated from each other, the flowable material is introduced between the stopper and the receptacle, and the stopper is placed back on the receptacle for capturing the flowable material sample.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A device for sampling a flowable material, said device comprising:
   a housing for receiving a receptacle therein, said housing sealing the receptacle from the ambient environment outside the housing;
   an opening formed in said housing;
   a device for opening and closing said opening, the receptacle being receivable into said housing through said opening when said opening is in an open condition, said device including a sealing element for sealing the opening when the device is in a closed condition;
   an inlet formed in said housing for receiving the flowable material therethrough;
   a first mechanism mounted within said housing for engaging one of the receptacle and a stopper for sealing the receptacle;
   a second mechanism mounted within the housing for engaging the other of the receptacle and the stopper, said second mechanism cooperating with said first mechanism to open the receptacle, close the receptacle or open and close the receptacle by removing the stopper, attaching the stopper or removing and attaching the stopper on the receptacle when the opening of the housing is in the closed condition.

2. The device according to claim 1, wherein said first mechanism is moveable with respect to said second mechanism along a longitudinal axis and/or rotatable around the longitudinal axis.

3. The device according to claim 2, wherein said first mechanism includes support rods having a longitudinal portion for holding, gripping and/or rotating the receptacle, said longitudinal portion of each of said support rods being offset from the longitudinal axis of said first mechanism.

4. The device according to claim 3, wherein said longitudinal portion has a non-skid surface formed as a part thereof or attached thereto on at least a surface facing the receptacle so as to better grip the receptacle.

5. The device according to claim 4, wherein said non-skid surface is non-skid tubing on the longitudinal portion of said support rods.

6. The device according to claim 1, wherein said first mechanism is mounted directly or indirectly to a shaft, said shaft being rotatable and/or moveable along a longitudinal axis, and wherein the first mechanism engages the receptacle.

7. The device according to claim 6, further comprising a flexible diaphragm barrier, one portion of said flexible diaphragm barrier being mounted to said housing to create a first seal with said housing and another portion of said flexible diaphragm barrier being mounted to said shaft to create a second seal with said shaft, said first and second seals allowing said shaft to be moved with the housing without a loss of integrity of the seal of the housing with outside ambient environment.

8. The device according to claim 1, further comprising an annular member, said annular member positioned such that when the receptacle is retracted to a filling position, the annular member is located above the receptacle so as to urge a major portion of the flowable sampled material into the mouth of the receptacle and to inhibit the flow down the sides of the receptacle and down to a lower portion of the housing.

* * * * *